United States Patent [19]

Terren et al.

[11] Patent Number: 5,804,216
[45] Date of Patent: Sep. 8, 1998

[54] ACIDIC COMPOSITION BASED ON LIPID VESICLES AND ITS USE IN TOPICAL APPLICATION

[75] Inventors: Nadia Terren, Chevilly Larue; Jacques Michelet, Champlan; Martine Perrin, Savigny sur Orge, all of France

[73] Assignee: L'Oreal, Paris, France

[21] Appl. No.: 605,921

[22] Filed: Feb. 23, 1996

[30] Foreign Application Priority Data

Feb. 23, 1995 [FR] France .................................. 95 02136

[51] Int. Cl.⁶ ........................ A61K 9/127; A61K 9/133; A61K 7/42; A61K 9/10
[52] U.S. Cl. ........................... 424/450; 424/59; 424/401; 428/402.2; 514/574; 514/845; 514/846; 514/859; 514/941
[58] Field of Search ........................... 428/402.2; 424/59, 424/450, 401; 514/574, 845, 941

[56] References Cited

U.S. PATENT DOCUMENTS

| | | | |
|---|---|---|---|
| 4,217,344 | 8/1980 | Vanlerberghe et al. | 424/60 |
| 4,897,308 | 1/1990 | Vanlerberghe et al. | 428/402.2 |
| 4,911,928 | 3/1990 | Wallach | 424/450 |
| 4,946,683 | 8/1990 | Forssen | 424/450 X |
| 5,229,104 | 7/1993 | Sottery et al. | 424/59 |
| 5,405,615 | 4/1995 | Mathur | 424/450 |
| 5,470,880 | 11/1995 | Yu et al. | 514/574 |
| 5,626,868 | 5/1997 | Morancais et al. | 424/450 |

FOREIGN PATENT DOCUMENTS

| | | |
|---|---|---|
| 0 433 132 A1 | 6/1991 | European Pat. Off. . |
| 0 043 327 A1 | 1/1982 | France . |
| 2 485 921 | 1/1982 | France . |
| 0 347 306 A1 | 12/1989 | France . |
| 0 382 619 A1 | 8/1990 | France . |
| 0 559 502 A1 | 9/1993 | France . |
| 0 582 503 A1 | 2/1994 | France . |
| 0 661 037 A1 | 7/1995 | France . |
| 40 05 711 C1 | 6/1991 | Germany . |
| WO 95/03781 | 2/1995 | WIPO . |

OTHER PUBLICATIONS

French Search Report Dated Jan. 5, 1996.

*Primary Examiner*—Richard D. Lovering
*Attorney, Agent, or Firm*—Oblon, Spivak, McClelland, Maier & Neustadt, P.C.

[57] ABSTRACT

A composition containing a dispersion of lipid vesicles with an aqueous core and/or of lipid vesicles with an oily core. At least one acidic compound is present in the dispersion in an amount which is sufficient to impart a pH of less than 5 to the composition. The lipid membrane of the vesicles with an aqueous core does not contain:

(a) acidic amphiphilic lipids
(b) or non-hydrogenated soya lecithin in the presence of glycerol in the dispersion.

The composition is stable and may be stored for several months.

30 Claims, No Drawings

0## ACIDIC COMPOSITION BASED ON LIPID VESICLES AND ITS USE IN TOPICAL APPLICATION

BACKGROUND OF THE INVENTION

1. Field of the Invention

The present invention relates to a composition having an acidic pH and comprising an aqueous dispersion of lipid vesicles, and to its use in topical application.

2. Discussion of the Background

Lipid vesicle dispersions are well known in the cosmetics field and in dermopharmacy.

Dispersions of lipid vesicles with an aqueous core, encapsulating an aqueous phase which may comprise water-soluble active substances which are protected from the external conditions, are known. These vesicles are obtained from ionic amphiphilic lipids and/or from nonionic amphiphilic lipids. They are disclosed in particular in EP-A 0,582,503 and EP-A 0,661,037.

EP-A 0,582,503 describes dispersions of lipid vesicles with an aqueous core, the lipid membrane of which consists of neutralized nonionic amphiphilic lipids and neutralized ionic amphiphilic lipids.

EP-A 0,661,037 describes dispersions of two types of lipid vesicles with an aqueous core which act in the deep layers and the surface layers of the epidermis, respectively.

Dispersions of lipid vesicles with an oily core, encapsulating an oily phase which may comprise liposoluble active substances which are thus protected from the external conditions, are also known. These vesicles with an oily core are described in particular in French patent applications Nos. 93/10588 and 94/12005.

Acidic compounds which are cosmetically or dermatologically active, such as hydroxy acids and $\alpha$- and $\beta$-keto acids, are increasingly used in the cosmetics field for face and/or body care. In particular, hydroxy acids are used more especially to give the face a glowing and sparkling complexion and thus a healthy, smooth and younger appearance, for the non-therapeutic treatment of wrinkles and/or fine lines on the skin and for removing comedones caused by acne. Unfortunately, because of their acidic nature these acidic compounds, and more particularly hydroxy acids, have the drawback of destabilizing certain supports and may have an irritant nature and lead to considerable discomfort.

SUMMARY OF THE INVENTION

The inventors have discovered, surprisingly, that it is possible to create stable acidic formulations (compositions) using acidic active agents with dispersions of lipid vesicles. Formulations comprising such dispersions exhibit, besides their stability, qualities of make-up application and of comfort which are specific to formulations based on vesicle systems.

This discovery is all the more surprising since lipid vesicles with an oily core or an aqueous core are, in principle, unstable in acidic medium. The reason for this is that they contain a lipid membrane which is liable to undergo hydrolysis in acidic medium.

Another subject of the invention relates to compositions intended to be applied topically. They are characterized in that they comprise a composition as defined above.

Another subject of the invention relates to the use of the compositions defined above as bases for facial and/or body care products or make-up (tinted cream, foundation, etc.).

These products may be in the form of dispersions which are more or less thickened, gels, creams, milks or sera.

The invention also relates to the use of the composition as defined above for the non-therapeutic treatment of comedones and wrinkles and/or fine lines on the skin, as well as to a process for the cosmetic treatment of comedones or wrinkles and/or fine lines on the skin, which comprises applying the composition of the invention to the skin.

Indeed, it has been observed in EP-A-0,582,503 that acidic dispersions of lipid vesicles with an aqueous core became unstable when the membrane contained acidic amphiphilic lipids (amphiphilic lipids containing at least one non-neutralized acidic function) which provided these dispersions with their acidity. Such dispersions could, however, be stabilized at a pH close to neutrality by incorporating neutralized amphiphilic lipids into the vesicle membrane.

It could thus be expected that the presence of an acidic compound in this type of vesicle dispersion, in an amount such that the pH of the dispersion is less than 5, would lead to the breakdown of the vesicles because it is in contact with their lipid membrane. However, the compositions based on a dispersion of lipid vesicles, in accordance with the present invention, which contain an acidic compound in an amount which is sufficient to make it possible to obtain a pH of less than 5 remain, unexpectedly, stable in acidic medium. They can be stored and used for the preparation of compositions for topical use.

DETAILED DESCRIPTION OF THE INVENTION

The present invention is thus more specifically directed to a composition comprising a dispersion of lipid vesicles with an aqueous core and/or of lipid vesicles with an oily core, the composition containing at least one acidic compound in an amount which is sufficient to impart a pH of less than 5 to the said composition, provided the lipid membrane of the vesicles with an aqueous core does not contain:

(a) acidic amphiphilic lipids
(b) or non-hydrogenated soya lecithin in the presence of glycerol in the dispersion.

The compositions in accordance with the present invention are, more particularly, oil-in-water dispersions in which the lipid vesicles act as dispersants of the oil in the aqueous continuous phase. The lipid vesicles according to the invention may encapsulate an aqueous phase (aqueous core) or an oily phase (oily core). Mixtures may be used. One specific form of the invention consists of a composition comprising an aqueous dispersion of vesicles with an oily core mixed with a dispersion of vesicles with an aqueous core encapsulating the acidic compound.

The acidic compound may be present in the aqueous phase of the dispersion of vesicles with an aqueous or oily core, or alternatively in the aqueous phase inside the vesicles with an aqueous core. In aqueous core vesicles, the acidic compound may be both inside the vesicle and in the outer aqueous phase.

When the composition is in the form of an aqueous dispersion of vesicles with an aqueous or oily core, the acidic compound is introduced into the external aqueous phase with stirring, in the vesicle dispersion already formed. When the composition is in the form of an aqueous dispersion of vesicles with an oily core and of vesicles with an aqueous core encapsulating the acidic compound, the acidic compound is introduced into a dispersion of vesicles with an oily core which is already formed by means of a dispersion of vesicles with an aqueous core encapsulating the water-soluble acidic compound.

The lipid vesicles with an aqueous core which are in accordance with the invention are vesicles comprising a lipid membrane obtained from nonionic amphiphilic lipids, from ionic amphiphilic lipids or from mixtures thereof. These vesicles are described in particular in EP 0,504,437 incorporated herein by reference and are prepared according to the processes described therein.

The lipid vesicles with an oily core which may be used in the invention are, in particular, oily globules in aqueous dispersion coated with a monolamellar or oligolamellar layer obtained from at least one lipophilic surfactant, a hydrophilic surfactant and either an ionic amphiphilic lipid or a fatty acid combined with a basic agent dissolved in the aqueous phase of the dispersion. The term "oligolamellar" layer is understood to refer to a layer comprising from 2 to 5 lipid lamellae. Examples of these vesicles are described in French patent applications Nos. 94/12005 and 93/10588 both incorporated herein by reference. They can be prepared according to a process of mixing, in a first step, with stirring, the oily phase comprising the hydrophilic surfactant, the lipophilic surfactant, the ionic amphiphilic lipid or the fatty acid and the aqueous phase optionally containing the basic agent, followed, in a second step, by subjecting the mixture obtained to homogenization based on the principle of cavitation. This homogenization is obtained either by means of, e.g., ultrasound, by means of high pressures of between 200 and 1500 bar, by means of homogenizers equipped with a rotor-stator head. etc.

Nonionic amphiphilic lipids used herein for the preparation of the vesicles with an aqueous core are preferably chosen from the group formed by:

(1) linear or branched polyglycerol ethers of formula:

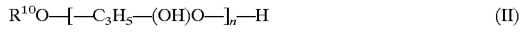

in which:

—$C_3H_5$ (OH)O is represented by the following structures, taken separately or as a mixture:

—$CH_2CHOHCH_2O$—;

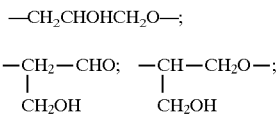

n is an average statistical value between 2 and 6;
$R^{10}$ represents:
(a) a linear or branched aliphatic chain containing from 12 to 18 carbon atoms;
(b) a residue $R^{11}CO$ where $R^{11}$ is a linear or branched $C_{11}$–$C_{17}$ aliphatic radical;
(c) a residue $R^{12}$—[—$OC_2H_3(R^{13})$—]—, where:
$R^{12}$ may take the meaning (a) or (b) given for $R^{10}$;
$OC_2H_3(R^{13})$— is represented by the following structures, taken separately or as a mixture:

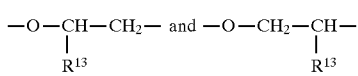

where $R^{13}$ takes the meaning (a) given for $R^{10}$;
(2) polyoxyethylenated fatty alcohols, polyoxyethylenated sterols;
(3) optionally polyoxyethylenated polyol esters;
(4) natural or synthetic glycolipids; and
(5) oxyethylenated polyglyceryl stearate.

The ionic amphiphilic lipids used according to the invention for the preparation of the lipid vesicles with an oily core or an aqueous core are preferably chosen from neutralized anionic lipids, amphoteric lipids and alkylsulphonic derivatives and more particularly from the group formed by:

alkaline salts of dicetyl phosphate and of dimyristyl phosphate, alkaline salts of cholesteryl sulphate, alkaline salts of cholesteryl phosphate, mono- and disodium acylglutamates and in particular the mono- and disodium salts of N-stearoylglutamic acid, the sodium salts of phosphatidic acid, the alkylsulphonic derivatives of formula:

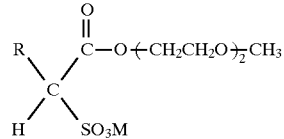

in which formula R represents the radicals $C_{16}H_{33}$ and $C_{18}H_{37}$ taken separately or as a mixture, and M is an alkali metal, phosphoaminolipids, natural phospholipids such as egg lecithin, soya lecithin, sphingomyelin, phosphatidylserine and dipalmitoylphosphatidylcholine and hydrogenated lecithins.

The vesicles with an aqueous core which are in accordance with the invention advantageously have an average diameter ranging from 10 to 1000 nm.

The vesicles with an aqueous core according to the invention are present in the composition in proportions ranging, preferably, from 0.5 to 15% by weight relative to the total weight of the composition.

A particularly preferred form of vesicles with an aqueous core consists of vesicles comprising a lipid membrane obtained from a mixture of polyoxyethylenated soya sterols and hydrogenated lecithin.

The lipophilic surfactants and the hydrophilic surfactants used for the preparation of the vesicles with an oily core each preferably contain at least one saturated fatty chain having more than approximately 12 carbon atoms. Even more preferably, this fatty chain contains from 16 to 22 carbon atoms.

According to another preferred embodiment of the invention, the lipophilic surfactant has an HLB of between approximately 2 and approximately 5. As is well known, the expression HLB (hydrophilic-lipophilic balance) is understood to refer to the equilibrium between the size and force of the hydrophilic group and the size and force of the lipophilic group of the surfactant. Examples of such lipophilic surfactants are sucrose distearate, diglyceryl distearate, glyceryl tristearate, decaglyceryl decastearate, diglyceryl monostearate, hexaglyceryl tristearate, decaglyceryl pentastearate, sorbitan monostearate, sorbitan tristearate, diethylene glycol monostearate, glyceryl palmitate, glyceryl stearate, glyceryl monostearate polyoxyethylenated with 2 EO (containing 2 mol of ethylene oxide), glyceryl monodebehenate, glyceryl dibehenate and pentaerythritol tetrastearate.

The hydrophilic surfactant preferably has an HLB of between approximately 8 and approximately 12.

The following compounds may be mentioned as examples of such hydrophilic surfactants: sorbitan monostearate polyoxyethylenated with 4 EO, sorbitan tristearate polyoxyethylenated with 20 EO, hexaglyceryl monostearate polyoxyethylenated with 8 EO, hexaglyceryl monostearate, methylglucose monostearate polyoxyethylenated with 10 EO, methylglucose distearate polyoxyethylenated with 12 EO and methylglucose distearate polyoxyethylenated with 20 EO.

According to the invention, the fatty acid is preferably chosen from $C_{16}$–$C_{22}$ saturated fatty acids. Mention may be made, for example, of palmitic acid, stearic acid, arachidic acid and behenic acid.

The basic agent contained in the aqueous phase of the dispersion of vesicles with an oily core, associated with fatty acid, is chosen, for example, from sodium hydroxide, triethanolamine, lysine and arginine.

Lipid vesicles in the form of an aqueous dispersion of oily globules coated with a layer obtained from sucrose distearate, from sorbitan monostearate oxyethylenated with 4 mol of ethylene oxide and from a disodium salt of acylglutamic acid are more particularly used.

The lipid vesicles with an oily core as described above preferably have an average size of less than 500 nanometers and more particularly of less than 200 nanometers.

The coated oily globules preferably represent 5 to 50% by weight relative to the total weight of the composition.

The compositions in accordance with the invention preferably have a pH of less than 5 and more particularly ranging from 2.8 to 4.8.

The acidic compounds present in the composition of the invention are preferably chosen from hydroxy acids and α- and β-keto acids.

Hydroxy acids which may be used in accordance with the present invention are preferably chosen from α-hydroxy acids, 5-η-octanoylsalicylic acid and salicylic acid. α-Hydroxy acids derived from fruit, such as glycolic acids, lactic acid, citric acid, tartaric acid, malic acid, mandelic acid or mixtures thereof, are more particularly used. Among these acids mentioned, lactic acid is very particularly preferred.

The amount of acidic compound present in the compositions of the invention preferably ranges from 0.1 to 10% by weight relative to the total weight of the composition and more preferably from 0.2 to 5% by weight and more particularly from 0.5 to 4% by weight.

The aqueous phase of the dispersion of the composition according to the invention may also contain a water-immiscible (oily) liquid dispersed by the lipid vesicles. The water-immiscible liquid, which may be present in the form of a dispersion in the aqueous phase of the dispersion, may be chosen in particular from the group formed by:

animal or plant oils formed by fatty acid esters and polyol esters, in particular liquid triglycerides, for example sunflower oil, corn oil, soya oil, marrow oil, grape seed oil, jojoba oil, sesame oil, walnut oil, fish oils and glyceryl tri-caprocaprylate, or plant or animal oils of formula $R_8COOR_9$, in which formula $R_8$ represents a higher fatty acid residue containing from 7 to 19 carbon atoms and $R_9$ represents a branched hydrocarbon chain containing from 3 to 20 carbon atoms, for example purcellin oil;

natural or synthetic essential oils such as, for example, eucalyptus oil, hybrid lavender oil, lavender oil, vetiver oil, Litsea cubeba oil, lemon oil, sandalwood oil, rosemary oil, camomile oil, savory oil, nutmeg oil, cinnamon oil, hyssop oil, caraway oil, orange oil, geraniol oil, prickly juniper oil and bergamot oil;

hydrocarbons such as hexadecane and liquid paraffin;

halocarbons, in particular fluorocarbons such as fluoroamines, for example perfluorotributylamine, fluorohydrocarbons, for example perfluorodecahydronaphthalene, fluoroesters and fluoroethers;

silicones, for example polysiloxanes, polydimethylsiloxanes and fluorosilicones;

inorganic acid esters of an alcohol; and ethers and polyethers.

The dispersion aqueous phase may also contain water-soluble, cosmetic and/or dermopharmaceutical active agents. The water-immiscible liquid may optionally contain a liposoluble active agent.

The dispersion aqueous phase may also contain adjuvants which have neither actual cosmetic activity nor actual dermopharmaceutical activity, but which are used for the formulation of the dispersion in the form of a lotion, cream or serum. These adjuvants are, in particular, taken from the group formed by the gelling agents, preserving agents, dyes, pigments, opacifying agents, fragrances, sunscreens and powders for cosmetic use.

Among the gelling agents which may be used, mention may be made of cellulose derivatives such as hydroxyethyl cellulose, sodium magnesium silicate or aluminium magnesium silicate, algae derivatives such as satiagum, natural gums such as tragacanth and synthetic polymers, in particular the mixture of isoparaffin polyacrylamide and lauryl alcohol oxyethylenated with 7 mol of ethylene oxide, sold under the name Sepigel 305 by the company Seppic.

The aqueous phase of the dispersion may contain soluble dyes, coated or uncoated nanotitaniums, nanopigments and dyes. Matte-effect powders may also be added. Mention may be made, for example, of starch powders, nylon powders, silica microspheres and flakes of mica coated with silica microspheres.

The term approximately as used herein means ±20%, preferably ±10%.

Other characteristics and advantages of the invention will emerge more clearly from the examples which follow, given by way of illustration and with no limitation being implied.

EXAMPLE 1

Foundation (dispersion of vesicles with an aqueous core, pH 3.3)

Phase $A_1$:

| | |
|---|---|
| Non-stabilized soya sterols oxyethylenated with 5 EO, sold under the name Generol 122E5 | 1.6 g |
| Hydrogenated lecithin sold under the name Lecinol S10 | 2.4 g |

Phase $A_2$:

| | |
|---|---|
| Sterile demineralized water | 15 g |

Phase $A_3$:

| | |
|---|---|
| Sterile demineralized water | 14 g |
| Methyl p-hydroxybenzoate | 0.2 g |
| Guanosine | 0.01 g |
| Glycerol | 3 g |
| Propylene glycol | 3 g |

Phase $B_1$:

| | |
|---|---|
| Palm oil | 6.5 g |
| Non-stabilized deodorized apricot kernel oil (oleic-linoleic acid triglycerides 66/28) | 9.5 g |
| Butyl p-hydroxybenzoate | 0.09 g |
| Propyl p-hydroxybenzoate | 0.1 g |

Phase $B_2$:

| | |
|---|---|
| Cyclopentadimethylsiloxane sold under the name Volatile Silicone 7158 | 10 g |

-continued

Phase B₃:

| | |
|---|---|
| Vitamin E acetate | 0.5 g |
| Stabilized 2-ethylhexyl 4-methoxycinnamate sold under the name Parsol MCX by Givaudan (sunscreen) | 1 g |

Phase C:

| | |
|---|---|
| Yellow iron oxide | 0.89 g |
| Yellow-brown iron oxide | 0.49 g |
| Black iron oxide | 0.11 g |
| Titanium oxide (anatase) | 5.51 g |

Phase D:

| | |
|---|---|
| Sterile demineralized water | 1 g |
| Preserving agent | 0.3 g |

Phase E:

| | |
|---|---|
| Sterile demineralized water | 18.84 g |
| Oxyethylenated (7 EO) mixture of polyacrylamide, isoparaffin and lauryl alcohol (gelling agent) in water (35.5/23/10.5/31), sold under the name Sepigel 305 | 2 g |

Phase F:

| | |
|---|---|
| Mixture of alpha-hydroxy acids derived from fruit (lactic acid/glycolic acid/citric acid 30/15/4) in water (pH = 2) | 1 g |

Phase G:

| | | |
|---|---|---|
| Starch crosslinked with octenylsuccinic anhydride, sold under the name Dry Flo | | 3 g |
| Sterile demineralized water | qs | 100 g |

Procedure

I—Preparation of the Vesicle Phase A

Preparation of $A_1$ in a manufacturing tank:

The water of part $A_1$ is introduced at 85° C. The oxyethylenated soya sterols (Generol 122 E5) are added with stirring. A viscous yellow oil is obtained. The hydrogenated lecithin is added with stirring for 15 min. A crumbly beige paste is obtained. The temperature is maintained at 85° C. with stirring.

Preparation of $A_3$ (melting pot):

The water of $A_3$ is introduced at 85° C.

The propylene glycol, glycerol and methyl p-hydroxybenzoate are added with stirring, using a Moritz stirrer, at 300 rpm. The guanosine is added, while maintaining the same stirring, until the guanosine is fully dissolved.

Preparation of the vesicle phase A:

$A_2$ (water) is added in 3 portions to $A_1$, at 85° C. with stirring, over 15 minutes. The mixture $A_1+A_2$ is left to swell for 1 hour.

$A_3$ (melting pot) is introduced, via the top of the tank, at 85° C. with stirring. Recycling is carried out, with stirring, for 10 minutes. The mixture is cooled to 55° C. with stirring.

High pressure homogenization run 3 runs on a high pressure homogenizer (500 bar) are carried out at 55° C. The scraped surface heat exchanger is set at 60° C.

First run: the product is recovered in the buffer tank.

Second run: the product is recovered in the buffer tank.

After the third run, the product is transferred to the manufacturing tank. It is cooled to 40° C. with stirring.

II—Preparation of $B_1+B_2+B_3$ (melting pot)

The palm oil, apricot kernel oil and butyl p-hydroxybenzoate are introduced. The mixture is heated at 80° C. with stirring, using a Moritz stirrer, at 500 rpm until homogenization is complete. It is cooled to 65° C. The volatile silicone is introduced via the bottom of the tank. The vitamin E acetate and sunscreen are added with stirring, using a Moritz stirrer, at 700 rpm. The mixture is cooled to 40° C.

III—Preparation of the Vesicle+Oils Dispersion

Part B (melting pot) is introduced, via the top of the tank, into the part A (manufacturing tank). Recycling is carried out, with stirring, for 10 min. The mixture is cooled to 25° C. with stirring.

6 runs are carried out on a high pressure homogenizer (500 bar). The heat exchanger is set to 30° C.

After the fourth run, the product is recovered in the buffer tank. After the fifth run, the product is recovered in the manufacturing tank. After the sixth run, the product is recovered in the buffer tank.

IV—Dispersion of the Pigments

About 400 kg of product are transferred from the buffer tank to the manufacturing tank and the pigments (phase C) are added. Recycling is carried out for 1 hour with stirring. The dispersion of C is checked with a microscope (there should be no lumps of pigment bigger than 30 microns).

The remainder of the product is transferred from the buffer tank to the manufacturing tank, with stirring. The temperature is maintained at 30° C.

V—Preparation of D

The preserving agent is dissolved in the water at room temperature.

VI—Preparation of E

The product Sepigel 305 is dispersed, at room temperature, using a deflocculating machine.

VII—Addition of the Phases D, E, F and G

D is added and homogenization is carried out with stirring for 5 minutes.

E is added and homogenization is carried out with stirring for 5 min. Correct dispersion of the gel is checked with a microscope. The mixture of alpha-hydroxy acids (phase F) and then the starch (G) are added with stirring for 5 min. The mixture is cooled to 25° C. with stirring, then the stirring is stopped. A control sample is taken.

The composition obtained is stable at room temperature after storage for 5 and a half months. It is also stable after storage for 2 months in an oven at 45° C.

EXAMPLE 2

Tinted Cream (dispersion of vesicles with an aqueous core, of 3.3)

Phase $A_1$:

| | |
|---|---|
| Soya sterols oxyethylenated with 5 EO, sold under the name Generol 122E5 | 1.6 g |
| Hydrogenated lecithin Lecinol S10 | 2.4 g |
| Sterile demineralized water | 3 g |

Phase $A_2$:

| | |
|---|---|
| Sterile demineralized water | 12 g |

-continued

| Phase A$_3$: | | |
|---|---|---|
| Sterile demineralized water | 14 g | |
| Methyl p-hydroxybenzoate | 0.2 g | |
| Guanosine | 0.01 g | |
| Propylene glycol | 3 g | |
| Phase A$_4$: | | |
| Glycerol | 3.0 g | |
| Non-stabilized biotechnological thermal plankton in aqueous dispersion | 1.12 g | |
| Phase C$_1$: | | |
| 2-Ethylhexyl 4-methoxycinnamate (Parsol MCX) | 4 g | |
| Butyl p-hydroxybenzoate | 0.05 g | |
| Propyl p-hydroxybenzoate | 0.1 g | |
| Phase C$_2$: | | |
| Cyclohexadimethylsiloxane sold under the name Dow Corning 246 Fluid | 8 g | |
| Cyclopentadimethylsiloxane (Volatile Silicone 7158) | 10 g | |
| Phase C$_3$: | | |
| Vitamin A palmitate | 0.25 g | |
| Phase C$_4$: | | |
| Fragrance | 0.3 g | |
| Phase D: | | |
| Sterile demineralized water | 1 g | |
| Preserving agent | 0.3 g | |
| Phase E: | | |
| Yellow iron oxide | 0.37 g | |
| Yellow-brown iron oxide | 0.34 g | |
| Black iron oxide | 0.09 g | |
| Titanium oxide (anatase) | 4.2 g | |
| Phase F: | | |
| Sterile demineralized water | 2 g | |
| D-Panthenol | 1 g | |
| Phase G: | | |
| Starch crosslinked with octenylsuccinic anhydride (Dry Flo) | 5 g | |
| Phase H: | | |
| Sterile demineralized water | 19.47 g | |
| Phase I: | | |
| Mixture of alpha-hydroxy acids derived from fruit (lactic acid/glycol acid/citric acid 30/15/4) in water | 1 g | |
| Phase J: | | |
| Sepigel 305 | 2.2 g | |
| Demineralized water | qs | 100 g |

The composition is prepared according to the same procedure as in Example 1. The vesicle phase A (A$_1$+A$_2$+A$_3$+A$_4$), the melting pot C (C$_1$+C$_2$+C$_3$+C$_4$), the preparation of the vesicle+oils dispersion and the addition of the phases D, E, F, G, H, I and J are carried out under the same conditions defined above.

The composition obtained is stable at room temperature after storage for 5 and a half months. It is also stable after storage for 2 months at 45° C.

EXAMPLE 3

Foundation (dispersion of vesicles with an aqueous core, pH 3.3)

| Phase A$_1$: | | |
|---|---|---|
| Generol 122 E5 | 1.6 g | |
| Lecinol S10 | 2.4 g | |
| Phase A$_2$: | | |
| Sterile demineralized water | 12 g | |
| Phase A$_3$: | | |
| Sterile demineralized water | 14 g | |
| Methyl p-hydroxybenzoate | 0.2 g | |
| Guanosine | 0.1 g | |
| Propylene glycol | 3 g | |
| Glycerol | 3 g | |
| Phase B$_1$: | | |
| Palm oil | 6.5 g | |
| Apricot kernel oil | 9.5 g | |
| Propyl p-hydroxybenzoate | 0.1 g | |
| Butyl p-hydroxybenzoate | 0.05 g | |
| Phase B$_2$: | | |
| Volatile Silicone 7158 | 10 g | |
| Phase B$_3$: | | |
| Vitamin E acetate | 0.5 g | |
| Parsol MCX | 1 g | |
| Phase C: | | |
| Yellow iron oxide | 0.89 g | |
| Yellow-brown iron oxide | 0.49 g | |
| Black iron oxide | 0.11 g | |
| Titanium oxide (anatase) | 5.51 g | |
| Phase D: | | |
| Sterile demineralized water | 1 g | |
| Preserving agent | 0.3 g | |
| Phase E: | | |
| Sterile demineralized water | 1 g | |
| Sepigel 305 | 0.3 g | |
| Phase F: | | |
| Lactic acid in water | 1 g | |
| Phase G: | | |
| Dry Flo | 3 g | |
| Sterile demineralized water | qs | 100 g |

The composition is prepared under the same conditions as those of Example 1. It is stable at room temperature.

EXAMPLE 4

Foundation (dispersion of vesicles with an oily core, pH 4.7)

| Phase A$_1$: | |
|---|---|
| Sucrose distearate (lipophilic surfactant) | 2.4 g |
| Sorbitan stearate oxyethylenated with 4 mol of ethylene oxide, sold by the company ICI under the name Tween 61 (hydrophilic surfactant) | 1.6 g |
| Disodium salt of N-stearoyl glutamic acid, sold by the company Ajinomoto under the name Acylglutamate HS 21 (ionic amphiphilic lipid) | 1.2 g |
| Stabilized mixture of sunflower, rose, nutmeg and blackcurrant pip oils (31/60/5.95/3) | 5 g |
| Hydrogenated isoparaffin (6-8 mol of isobutylene) | 9 g |
| Polydimethylsiloxane sold under the name Dow Corning Fluid 200-5CST by Dow Corning | 9 g |
| Vitamin E (D,L-α-tocopherol) | 0.09 g |
| Parsol MCX | 1.0 g |
| Phase A$_2$: | |
| Sterile demineralized water | 35 g |

-continued

| | |
|---|---|
| Disodium salt of ethylenediaminetetraacetic acid (EDTA) dihydrate | 4 g |
| Glycerol | 3 g |
| Phase $B_1$: | |
| Sterile demineralized water | 11.85 g |
| Sodium and magnesium silicate | 0.3 g |
| Phase $B_2$: | |
| Yellow iron oxide | 1.11 g |
| Yellow-brown iron oxide | 0.47 g |
| Black iron oxide | 0.17 g |
| Titanium oxide (anatase) | 4.25 g |
| Nano (titanium oxide) (anatase treated with 4.9/0.6 alumina/silica) | 3 g |
| Phase C: | |
| Sterile demineralized water | 1 g |
| Preserving agent | 0.3 g |
| Phase D: | |
| Polyethylene glycol containing 8 mol of ethylene oxide | 5 g |
| Phase E: | |
| Matt-effect powder | 2 g |
| Phase F: | |
| Sepigel 305 | 1.2 g |
| Phase G: | |
| Mixture of α-hydroxy acids: lactic acid/glycolic acid/citric acid (30/15/4) in water | 1 g |
| Sterile demineralized water | qs 100 g |

Procedure

I—Manufacture of the Vesicle Phase A

Phase $A_1$ is melted at 85°–90° C.

Homogenization is carried out.

In parallel, phase $A_2$ is prepared (dissolution of the EDTA) and is brought to 60° C.

Phase $A_2$ is poured onto phase $A_1$ quickly and with vigorous stirring. The mixture is homogenized at 60° C. for 10 min. The mixture is run on the high pressure homogenizer at 500 bar. A minimum of 2 runs are necessary. A diameter of 200 nm must be obtained for a polydispersity of less than 1.

The mixture is cooled to 30° C. and de-aerated.

II—Preparation of the Pigment Dispersion

In parallel, the sodium magnesium silicate gel is prepared, using a homogenizer.

The gel is introduced into the manufacturing tank. The pigments and the nanotitaniums (phase $B_2$) are dispersed therein. The mixture is cooled to 35° C. over 15 min. Phase C (preserving agent) is introduced.

Dispersion is continued for one-and-a-half hours in total.

III—Dispersion of the Vesicle Dispersion in the Pigment Dispersion

The vesicle phase is introduced at 30° C., in several portions, into the pigment dispersion via the bottom of the tank with high speed stirring using a paddle turbomixer.

The turbomixing is continued for 1 hour. The phase D is added by gravity. The mixture is homogenized for 5 minutes. Phase E (powder) is added and the mixture is homogenized for 2 minutes. Phase F (gelling agent) is added and the mixture is homogenized for 10 minutes. De-aeration is carried out to the maximum.

IV—Introduction of the Alpha-Hydroxy Acids

Phase G is added, with high speed paddle stirring, to the formula thus obtained in gel form. The mixture is homogenized for 5 minutes.

The composition obtained is stable at room temperature.

EXAMPLE 5

Foundation (dispersion of vesicles with an oily core, of pH 4.7)

| | |
|---|---|
| Phase $A_1$: | |
| Sucrose distearate | 2.4 g |
| Tween 61 | 1.6 g |
| Acylglutamate HS 21 | 1.2 g |
| Mixture of sunflower, rose, nutmeg and blackcurrant pip oils (31/60/5.95/3) | 5 g |
| Hydrogenated isoparaffin | 9 g |
| Dow Corning Fluid 200-5 CST | 9 g |
| Vitamin E | 0.09 g |
| Parsol MCX | 1 g |
| Phase $A_2$: | |
| Sterile demineralized water | 35 g |
| EDTA | 0.05 g |
| Glycerol | 4 g |
| Phase $B_1$: | |
| Sterile demineralized water | 11.85 g |
| Sodium magnesium silicate | 0.3 g |
| Phase $B_2$: | |
| Yellow iron oxide | 1.11 g |
| Yellow-brown iron oxide | 0.47 g |
| Black iron oxide | 0.17 g |
| Nano (titanium oxide) | 3 g |
| Titanium oxide (anatase) | 4.25 g |
| Phase C: | |
| Sterile demineralized water | 1 g |
| Preserving agent | 0.3 g |
| Phase D: | |
| Polyethylene glycol (80 EO) | 5 g |
| Phase E: | |
| Matt-effect powder | 2 g |
| Phase F: | |
| Sepigel 305 | 1.2 g |
| Phase G: | |
| Lactic acid in water | 1 g |
| Sterile demineralized water | qs 100 g |

The composition is obtained according to the same process as that of Example 4. It is stable at room temperature.

EXAMPLE 6

Foundation (dispersion of vesicles with an oily core and of vesicles with an aqueous core encapsulating the α-hydroxy acids, pH 4.7)

| | |
|---|---|
| Phase $A_1$: | |
| Sucrose distearate | 1.8 g |
| Tween 61 | 1.20 g |
| Acylglutamate HS21 | 0.90 g |
| Mixture of sunflower, rose, nutmeg and blackcurrant pip oils (31/60/5.95/3) | 3.70 g |

13
-continued

| | |
|---|---|
| Hydrogenated isoparaffin (8 EO) | 6.70 g |
| Dow Corning Fluid 200-5 CST | 6.70 g |
| Vitamin E | 0.06 g |
| Parsol MCX | 0.70 g |
| Phase A$_2$: | |
| Sterile demineralized water | 26.12 g |
| Disodium EDTA | 0.03 g |
| Glycerol | 2.98 g |
| Phase B$_1$: | |
| Sterile demineralized water | 7.24 g |
| Sodium magnesium silicate | 0.22 g |
| Phase B$_2$: | |
| Yellow iron oxide | 0.83 g |
| Yellow-brown iron oxide | 0.35 g |
| Black iron oxide | 0.13 g |
| Titanium oxide (anatase) | 3.17 g |
| Nano(titanium oxide) of Example 4 | 2.24 g |
| Phase C: | |
| Demineralized water | 0.74 g |
| Preserving agent | 0.22 g |
| Phase D: | 2 g |
| Polyethylene glycol (8 EO) | 3.73 g |
| Phase E: | 1.2 g |
| Matt-effect powder | 1.49 g |
| Phase F: | |
| Sepigel 305 | 0.89 g |
| Phase G$_1$: | |
| Generol 122 E5 | 1.20 g |
| Lecinol S10 | 1.8 g |
| Sterile demineralized water | 11.20 g |
| Phase G$_2$: | |
| Sterile demineralized water | 10.45 g |
| Methyl p-hydroxybenzoate | 0.07 g |
| Propylene glycol | 2.24 g |
| Lactic acid/glycolic acid/citric acid mixture (36/15/4) in water, pH = 2 | 0.75 g |
| Sterile demineralized water | qs 100 g |

Procedure

The dispersion of vesicles with an oily core is prepared from phases A$_1$, A$_2$, B$_1$, B$_2$, C, D, E and F according to the same steps of the process of Example 4 preceding the introduction of the α-hydroxy acids.

A vesicle phase with an aqueous core (phase G$_1$) is prepared, into which the phase G$_2$ containing the α-hydroxy acids is added during the second hydration.

This vesicle phase is then considered as active and is added, with high speed paddle stirring, to the dispersion of vesicles with an oily core already formed.

The composition obtained is stable at room temperature.

This application is based on French patent application 95-02136 filed Feb. 23, 1995, incorporated herein by reference.

What is claimed as new and desired to be secured by Letters Patent of the United States is:

1. A composition comprising an aqueous dispersion of lipid vesicles having an oily core, or a mixture of lipid vesicles having an aqueous core and lipid vesicles having an oily core, said composition further comprising at least one acidic compound in an amount which is sufficient to impart a pH of less than 5 to the said composition, provided that a lipid membrane of the vesicles with an aqueous core does not contain acidic amphiphilic lipids, and does not contain non-hydrogenated soya lecithin when the dispersion comprises glycerol.

2. The composition according to claim 1, wherein said dispersion is an oil-in-water dispersion and where the lipid vesicles serve as dispersants of oil in the aqueous phase of the dispersion.

3. The composition according to claim 1, comprising a dispersion of vesicles with an oily core mixed with a dispersion of vesicles with an aqueous core, the aqueous core vesicles encapsulating the acidic compound.

4. The composition according to claim 1, wherein the acidic compound is present in the aqueous phase of the dispersion.

5. The composition according to claim 1, comprising vesicles with an oily core wherein the acidic compound is present in the aqueous phase of the dispersion of vesicles with an oily core and is there introduced by the addition of a dispersion of vesicles with an aqueous core encapsulating the acidic compound.

6. The composition according to claim 5, wherein the vesicles with an aqueous core comprise a lipid membrane comprising nonionic amphiphilic lipids, ionic amphiphilic lipids or mixtures thereof.

7. The composition according to claim 6, wherein the ionic amphiphilic lipids are neutralized anionic lipids, amphoteric lipids or alkylsulphonic derivatives.

8. The composition according to claim 7, wherein the ionic amphiphilic lipids are selected from the group consisting of:

alkaline salts of dicetyl phosphate and of dimyristyl phosphate, alkaline salts of cholesteryl sulphate, alkaline salts of cholesteryl phosphate, mono- and disodium acylglutamates, the sodium salts of phosphatidic acid, the alkylsulphonic derivatives of formula:

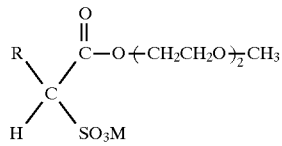

in which formula R represents the radicals $C_{16}H_{33}$ and $C_{18}H_{37}$ taken separately or as a mixture, and M is an alkali metal, phosphoaminolipids, and natural phospholipids.

9. The composition according to claim 6, comprising a nonionic amphiphilic lipid selected from the group consisting of:

(1) linear or branched polyglycerol ethers of formula:

$$R^{10}O-[-C_3H_5-(OH)O-]_n-H \qquad (II)$$

in which:

—$C_3H_5(OH)O$ is represented by the following structures, taken separately or as a mixture:

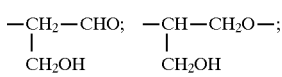

n is an average statistical value between 2 and 6;

$R^{10}$ represents:
 (a) a linear or branched aliphatic chain containing from 12 to 18 carbon atoms;
 (b) a residue $R^{11}CO$ where $R^{11}$ is a linear or branched $C_{11}$–$C_{17}$ aliphatic radical;
 (c) a residue $R^{12}$—[—$OC_2H_3(R^{13})$—]—, where:
 $R^{12}$ may take the meaning (a) or (b) given for $R^{10}$;
 $OC_2H_3(R^{13})$— is represented by the following structures, taken separately or as a mixture:

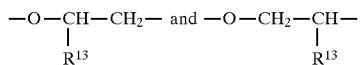

where $R^{13}$ takes the meaning (a) given for $R^{10}$;
 (2) polyoxyethylenated fatty alcohols, polyoxyethylenated sterols;
 (3) optionally polyoxyethylenated polyol esters;
 (4) natural or synthetic glycolipids; and
 (5) oxyethylenated polyglyceryl stearate.

10. The composition according to claim 1, comprising vesicles with an oily core which are individually coated with a monolamellar or oligolamellar layer obtained from at least one lipophilic surfactant, a hydrophilic surfactant and either an ionic amphiphilic lipid or a fatty acid combined with a basic agent dissolved in the aqueous phase of the dispersion.

11. The composition according to claim 10, wherein the lipophilic and hydrophilic surfactants contain a fatty chain having more than 12 carbon atoms.

12. The composition according to claim 11, wherein the lipophilic surfactant is selected from the group consisting of sucrose distearate, diglyceryl distearate, tetraglyceryl tristearate, decaglyceryl decastearate, diglyceryl monostearate, hexaglyceryl tristearate, decaglyceryl pentastearate, sorbitan monostearate, sorbitan tristearate, diethylene glycol monostearate, glyceryl palmitate, glyceryl stearate, glyceryl monostearate polyoxyethylenated with 2 EO (containing 2 mol of ethylene oxide), glyceryl monobehenate, glyceryl dibehenate and pentaerythritol tetrastearate.

13. The composition according to claim 11, wherein the hydrophilic surfactant is selected from the group consisting of sorbitan monostearate polyoxyethylenated with 4 EO, sorbitan tristearate polyoxyethylenated with 20 EO, hexaglyceryl monostearate polyoxyethylenated with 8 EO, hexaglyceryl monostearate, methylglucose monostearate polyoxyethylenated with 10 EO, methylglucose distearate polyoxyethylenated with 12 EO and methylglucose distearate polyoxyethylenated with 20 EO.

14. The composition according to claim 10, wherein the lipophilic surfactant has an HLB of between approximately 2 and approximately 5 and wherein the hydrophilic surfactant has an HLB of between approximately 8 and approximately 12.

15. The composition according to claim 10, wherein the fatty acid is a saturated $C_{16}$–$C_{22}$ fatty acid.

16. The composition according to claim 10, wherein the basic agent associated with the fatty acid is selected from the group consisting of sodium hydroxide, triethanolamine, lysine and arginine.

17. The composition according to claim 10, wherein the vesicles with an oily core comprise a lipid membrane obtained from sucrose distearate, from sorbitan monostearate oxyethylenated with 4 mol of ethylene oxide and from a disodium salt of acylglutamic acid.

18. The composition according to claim 1, wherein the vesicles with an aqueous core comprise a lipid membrane obtained from oxyethylenated soya sterols and hydrogenated lecithin.

19. The composition according to claim 1, wherein the vesicles with an aqueous core are present in proportions ranging from 0.5 to 15% by weight relative to the total weight of the composition.

20. The composition according to claim 1, comprising vesicles with an oily core in proportions ranging from 0.5 to 50% by weight relative to the total weight of the composition.

21. The composition according to claim 1, wherein the pH is from 2.8 to 4.8.

22. The composition according to claim 1, wherein the acidic compound is selected from a group consisting of hydroxy acids and α- and β-keto acids.

23. The composition according to claim 22, comprising a hydroxy acid chosen from the group consisting of α-hydroxy acids, salicylic acid and 5-η-octanoylsalicylic acid.

24. The composition according to claim 23, comprising a α-hydroxy acid selected from the group consisting of glycolic acid, tartaric acid, malic acid, citric acid, mandelic acid lactic acid and mixtures thereof.

25. The composition according to claim 24, comprising lactic acid.

26. The composition according to claim 1, wherein the acidic compound is present in proportions ranging from 0.1 to 10% by weight relative to the total weight of the composition.

27. The composition according to claim 1, further comprising a water-immiscible liquid dispersed in the aqueous phase of the dispersion by the lipid vesicles.

28. The composition according to claim 1, wherein the aqueous phase of the dispersion further comprises an adjuvant selected from the group consisting of gelling agents, preserving agents, pigments, dyes, opacifying agents, fragrances, and cosmetically or dermopharmaceutically active agents.

29. A composition for topical use comprising, the composition as defined in claim 1.

30. A process for the treatment of skin including comedones, wrinkles and fine lines on the skin, comprising applying a composition according to claim 1 to the skin.

* * * * *